(12) United States Patent
Hodson (10) Patent No.: US 7,299,801 B2
(45) Date of Patent: *Nov. 27, 2007

(54) METERING VALVE FOR A METERED DOSE INHALER PROVIDING CONSISTENT DELIVERY

(75) Inventor: Peter D. Hodson, Breaston (GB)

(73) Assignee: 3M Innovative Properties Company, St. Paul, MN (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/655,419

(22) Filed: Sep. 4, 2003

(65) Prior Publication Data

US 2004/0139966 A1 Jul. 22, 2004

Related U.S. Application Data

(60) Provisional application No. 60/408,637, filed on Sep. 6, 2002.

(51) Int. Cl.
*A61M 11/00* (2006.01)

(52) U.S. Cl. .............................. 128/200.23; 128/205.24

(58) Field of Classification Search ........... 128/200.23, 128/200.24, 203.12, 203.15, 203.19, 203.22, 128/203.24, 205.24; 251/353, 354; 222/402.1, 222/182, 402.2, 394, 402.24

See application file for complete search history.

(56) References Cited

U.S. PATENT DOCUMENTS

| 1,800,156 | A |   | 4/1931  | Rotheim |          |
|-----------|---|---|---------|---------|----------|
| 1,892,750 | A |   | 1/1933  | Rotheim |          |
| 2,723,055 | A |   | 11/1955 | Beard, Jr. | ................... 222/394 |
| 3,123,261 | A |   | 3/1964  | Gorman |          |
| 3,385,482 | A |   | 5/1968  | Frangos | .................... 222/402.2 |
| 3,405,846 | A |   | 10/1968 | Klun |          |
| 3,547,405 | A | * | 12/1970 | Ewald | .......................... 251/354 |
| 3,592,357 | A |   | 7/1971  | Welch | .......................... 222/193 |
| 3,727,806 | A |   | 4/1973  | Wilmot |          |
| 3,741,446 | A |   | 6/1973  | Marand | ....................... 222/402 |
| 4,362,257 | A |   | 12/1982 | Shay |          |
| 4,427,137 | A | * | 1/1984  | Dubini | .................... 222/402.2 |
| 4,798,226 | A |   | 1/1989  | Struth | ...................... 137/512.4 |
| 4,819,834 | A |   | 4/1989  | Thiel | ........................... 222/355 |
| 4,858,790 | A |   | 8/1989  | Howlett | .................... 222/402.2 |
| 4,953,759 | A |   | 9/1990  | Schmidt | .................... 222/402.2 |
| 5,085,351 | A |   | 2/1992  | Martin | ........................ 222/287 |
| 5,169,038 | A |   | 12/1992 | Di Giovanni | ............ 222/402.2 |
| 5,400,920 | A |   | 3/1995  | Barnhart | ......................... 222/1 |
| 5,477,992 | A |   | 12/1995 | Jinks et al. | .............. 222/402.2 |
| 5,484,088 | A |   | 1/1996  | Martin | ..................... 222/402.2 |
| 5,703,187 | A |   | 12/1997 | Timmers | ..................... 526/282 |

(Continued)

FOREIGN PATENT DOCUMENTS

EP 0 061 973 B1 10/1982

(Continued)

*Primary Examiner*—Steven O. Douglas (57) ABSTRACT

The present invention relates to a novel design for a metering valve that provides improved consistency of formulation delivery. Generally, the metering valve includes (a) a valve stem that generally defines a longitudinal axis and includes a body portion having a metering surface, wherein the longitudinal axis and a plane tangential to at least a portion of the metering surface define an angle from about 2° to about 90°; and (b) a valve body having an internal chamber defined at least in part by the body wall and includes a metering portion configured to substantially conform to the metering surface of the valve stem.

19 Claims, 10 Drawing Sheets

U.S. PATENT DOCUMENTS

| | | | |
|---|---|---|---|
| 5,772,085 A | 6/1998 | Bryant et al. | 222/402.2 |
| 5,938,085 A | 8/1999 | Conroy et al. | 222/402.2 |
| 5,983,927 A | 11/1999 | Simon et al. | 137/516 |
| 6,112,950 A | 9/2000 | Di Giovanni et al. | 222/402.1 |
| 6,123,237 A | 9/2000 | Lasserre et al. | 222/402 |
| 6,345,740 B1 * | 2/2002 | Riebe | 222/402.1 |
| 6,729,351 B2 * | 5/2004 | Bircann et al. | 137/630.14 |
| 6,737,044 B1 * | 5/2004 | Dickinson et al. | 424/46 |
| 6,782,886 B2 * | 8/2004 | Narayan et al. | 128/200.14 |
| 2004/0139965 A1 * | 7/2004 | Greenleaf et al. | 128/200.23 |

FOREIGN PATENT DOCUMENTS

| | | |
|---|---|---|
| EP | 0 567 348 B1 | 10/1993 |
| EP | 0 801 009 B1 | 10/1997 |
| FR | 1.225.163 | 6/1960 |
| FR | 1.461.685 | 2/1966 |
| GB | 1035304 | 7/1966 |
| GB | 1 201 918 | 8/1970 |
| GB | 1 524 293 | 9/1978 |
| GB | 2 004 526 A | 4/1979 |
| GB | 2 086 845 A | 5/1982 |
| GB | 2 206 100 A | 12/1988 |
| WO | WO 92/11190 | 7/1992 |
| WO | WO 93/22221 | 11/1993 |
| WO | WO 95/03984 | 2/1995 |
| WO | WO 99/20664 | 4/1999 |
| WO | WO 03/000570 A1 | 1/2003 |

* cited by examiner

METERING VALVE FOR A METERED DOSE INHALER PROVIDING CONSISTENT DELIVERY

CROSS-REFERENCE TO RELATED APPLICATION

This application claims priority to U.S. Provisional Patent Application No. 60/408,637, filed Sep. 6, 2002.

BACKGROUND

Metering valves are a common means by which aerosols are dispensed from aerosol containers. Metering valves are particularly useful for administering medicinal formulations that include a liquefied gas propellant and are delivered to a patient in an aerosol.

When administering medicinal formulations, a dose of formulation sufficient to produce the desired physiological response is delivered to the patient. The proper predetermined amount of the formulation must be dispensed to the patient in each successive dose. Thus, any dispensing system must be able to dispense doses of the medicinal formulation accurately and reliably to help assure the safety and efficacy of the treatment.

Metering valves have been developed to provide control over the dispensing of medicinal aerosol formulations. A metering valve may be used to regulate the volume of a medicinal formulation passing from a container to a metering chamber, which defines the maximum amount of the formulation that will be dispensed as the next dose. Reliable and controllable flow of the medicinal formulation into the metering chamber may contribute to the accuracy and/or precision of the metering of successive doses of the formulation. Thus, reliable and controllable flow of the medicinal formulation into the metering chamber may improve performance of the metering valve and, therefore, may be highly desirable.

In some metering valves, the metering chamber fills with the medicinal formulation prior to the patient actuating the valve stem and thereby releasing the dose. The metering chamber is refilled with formulation after dispensing one dose so that the metering valve is ready to discharge the next dose. Consequently, the metering chamber contains formulation at all times except for the brief time during which the valve stem is depressed by the user to discharge a dose. Also, the passageways through which the formulation must flow to reach the metering chamber are often narrow and tortuous. As a result, metering valves configured in this way have a number of disadvantages resulting in, for example, erratic dosing due to loss of prime. "Loss of prime" means the occurrence of vapor or air voids in the metered volume, thereby leading to a shortfall in the volume of dose being metered by the valve. A principal cause of loss of prime is the presence of restrictions in the entry passageway or passageways through which formulation must pass to fill the metering chamber. Such restrictions can lead to flow disruption and thus also to the occurrence of vapor or air voids in the metering chamber.

Another phenomenon that can lead to erratic dosing is loss of dose. "Loss of dose" means a change in the amount of suspended drug or excipient particles in a metered dose of formulation, compared to the average composition of the bulk formulation in the container. A principal cause of loss of dose is the settling of drug particles into, or their movement out of, restricted regions of the metering valve such that the proper concentration of formulation cannot subsequently be obtained within the restricted regions prior to dose delivery. For example, drug particles may settle in a residual metering volume—any part of the metering valve bounded by a metering surface and that, when the metering valve is in the resting position, remains fluid filled but is not in substantially free-flowing communication with the bulk formulation.

In other metering valves, residual metering volume may be limited to some extent by designing the metering valve so that the metering chamber does not materialize unless and until the valve stem is actuated. However, even in these metering valves, a small residual metering volume exists when the metering valve is at rest because a small annular gap exists between the valve stem and the metering valve body.

Actuation of these valve stems can be divided into a filling stage and a discharge stage. The filling stage begins as the valve stem is depressed during actuation. The action of depressing the valve stem causes the formation of a transient metering chamber, which is in fluid communication with the residual metering volume defined by the small annular gap. As the valve stem is depressed, the transient portion of the metering chamber expands and formulation enters the metering chamber. As displacement of the valve stem continues, a stage is reached at which filling of the transient metering chamber stops.

Eventually, displacement of the valve stem continues to the discharge stage, in which the metered formulation is discharged. In these valves, a single actuation thus causes rapid filling of the transient metering chamber followed by discharge of the formulation to the patient. Generally, metered formulation does not reside for any appreciable length of time in the metering chamber in these metering valves. However, some formulation may reside in the residual metering volume defined by the small annular gap when the metering valve is at rest.

Some metering valves limit the height of the annular gap, thereby reducing the residual volume and limiting the amount of formulation that resides in the metering chamber between actuation events.

While a metering valve having a transient metering chamber provides advantages over other types of metering valves for the delivery of aerosol formulations, the flow of formulation from the container to the metering chamber may be disrupted. Disrupted flow of formulation refers to filling a metering chamber through one or more bottleneck regions of significantly restricted access. Flow through the bottleneck regions may be impeded sufficiently to give rise to substantially incomplete filling of the metering chamber, particularly under conditions typical of patient use. When this happens, formulation may be delivered in inconsistent or inaccurate doses. Of course, all metering chamber inlets become significantly restricted immediately prior to being sealed off during actuation. Disrupted flow, as just described, refers to flow access during the majority of the filling stage of actuation.

Certain metering valves have been designed to improve the flow of formulation into the metering chamber. For example, some metering valves include angled spillway filling channels designed to limit disruption of the flow of formulation into the metering chamber. Less disrupted flow may decrease the likelihood and extent to which vapor or air voids form in the metered volume and, therefore improve performance of the metering valve.

SUMMARY OF THE INVENTION

The present invention relates to a novel design for a metering valve that provides improved consistency of formulation delivery. The metering valve of the present invention includes a valve stem designed to (1) limit or eliminate the residual metering volume, thereby reducing the amount of formulation that resides in the metering chamber while the metering valve is at rest, and (2) limit restrictions on the free flow of formulation into the metering chamber. Consequently, consistent delivery of formulation is obtained by reducing the effects of loss of prime and loss of dose.

The present invention provides an aerosol metering valve that includes a valve stem that generally defines a longitudinal axis, a valve body, and a metering gasket configured to be able to form a transient, substantially fluid-tight face seal between the valve stem and a sealing portion of the valve body. The valve stem includes a body portion including a proximal end, a distal end, and at least one side surface connecting the proximal end and the distal end and including a metering surface, wherein the longitudinal axis and a plane tangential to at least a portion of the metering surface define an angle from about 2° to about 90°.

DETAILED DESCRIPTION OF THE INVENTION

The following description is set forth in terms of an aerosol metering valve used to dispense an aerosol formulation from an aerosol container. However, the metering valve and methods of the present invention have application to virtually any pressurized fluid requiring delivery of an accurate, metered dose. In particular, the metering valves described herein are useful for dispensing medicinal aerosol formulations.

When used to dispense medicinal aerosol formulations, a metering valve according to the present invention may be used to administer virtually any aerosol formulation of drug into a body cavity of a patient, such as the mouth, nose, anus, vagina, ears, or onto the eyes or any skin area of the patient. However, the present invention is not limited to medicinal applications and may be used wherever a precise amount of material from a pressurized fluid is to be delivered to a given region.

Figure 1:
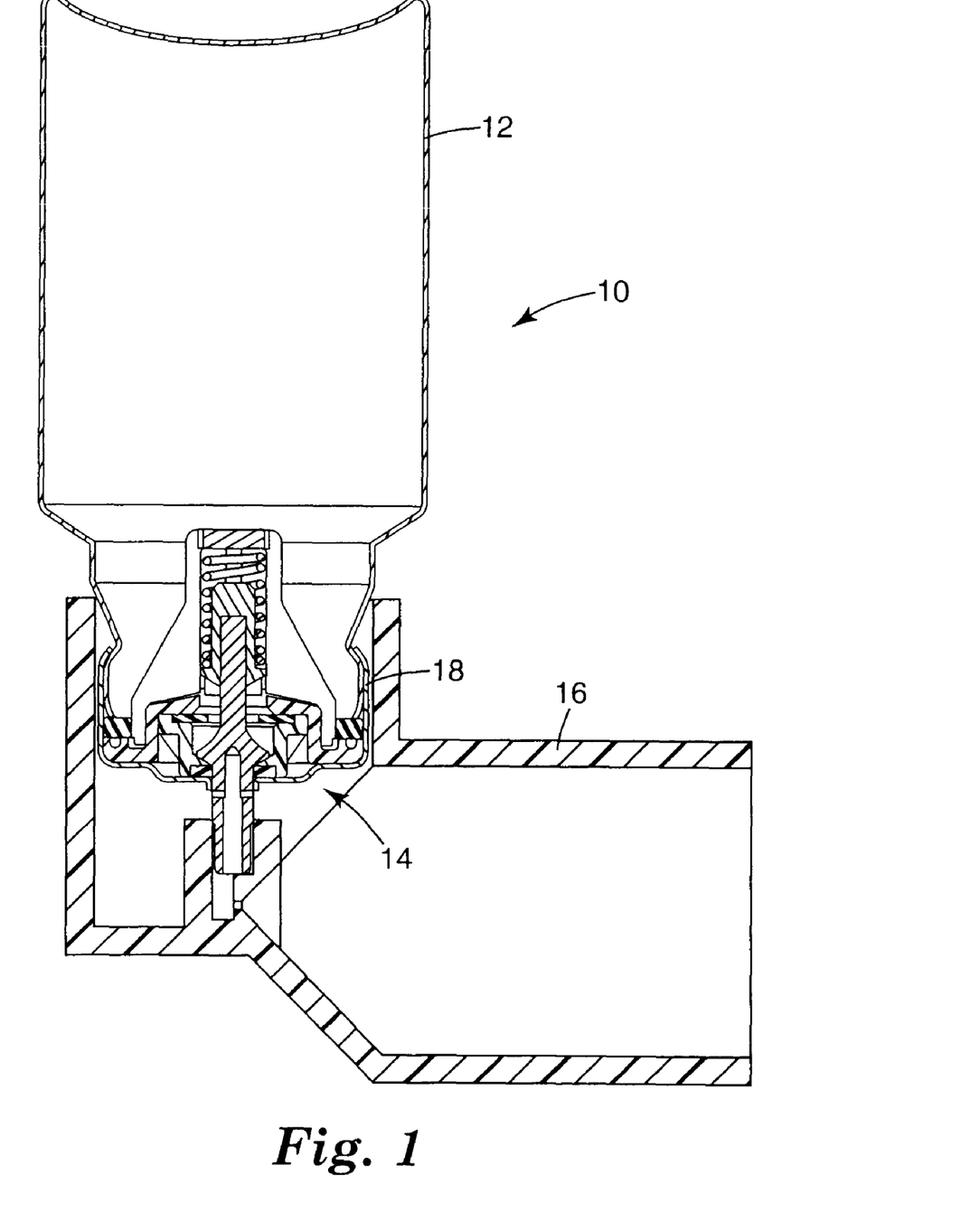
FIG. 1 is a cross-sectional view of a metered dose inhaler including an embodiment of the aerosol metering valve according to the present invention.

FIG. 1 shows an aerosol dispensing apparatus, generally designated as 10, that incorporates one embodiment of a metering valve 14 according to the present invention. The top end of the metering valve 14 is crimped around the end of a conventional aerosol container 12, while a conventional discharge piece 16 is mounted around the bottom of the metering valve 14. Thus, aerosol formulation is dispensed downwardly from the aerosol container 12, through the metering valve 14, then through the discharge piece 16 where it is delivered to a patient. The discharge piece 16 directs the aerosol formulation toward the body cavity or skin area to which the formulation is to be delivered. For example, discharge piece 16 may be a mouthpiece that can be inserted into the patient's mouth, thereby providing oral administration of the aerosol formulation.

The aerosol-dispensing device shown in FIG. 1 is merely one example of how a metering valve according to the present invention can be incorporated into a dispensing apparatus. Furthermore, the configuration of the discharge piece 16 depends upon the application for the aerosol.

In many of the figures, a metering valve or valve stem is shown in isolation for ease of additional components to form a metering valve. Such metering valves, as well as metering valves shown in isolation in the figures, may be combined with one or more additional components to form an aerosol dispensing device. It is understood that any particular feature shown in a metering valve and/or valve stem embodiment may be combined with features shown in other embodiments and/or incorporated appropriately within other embodiments.

Figure 2:
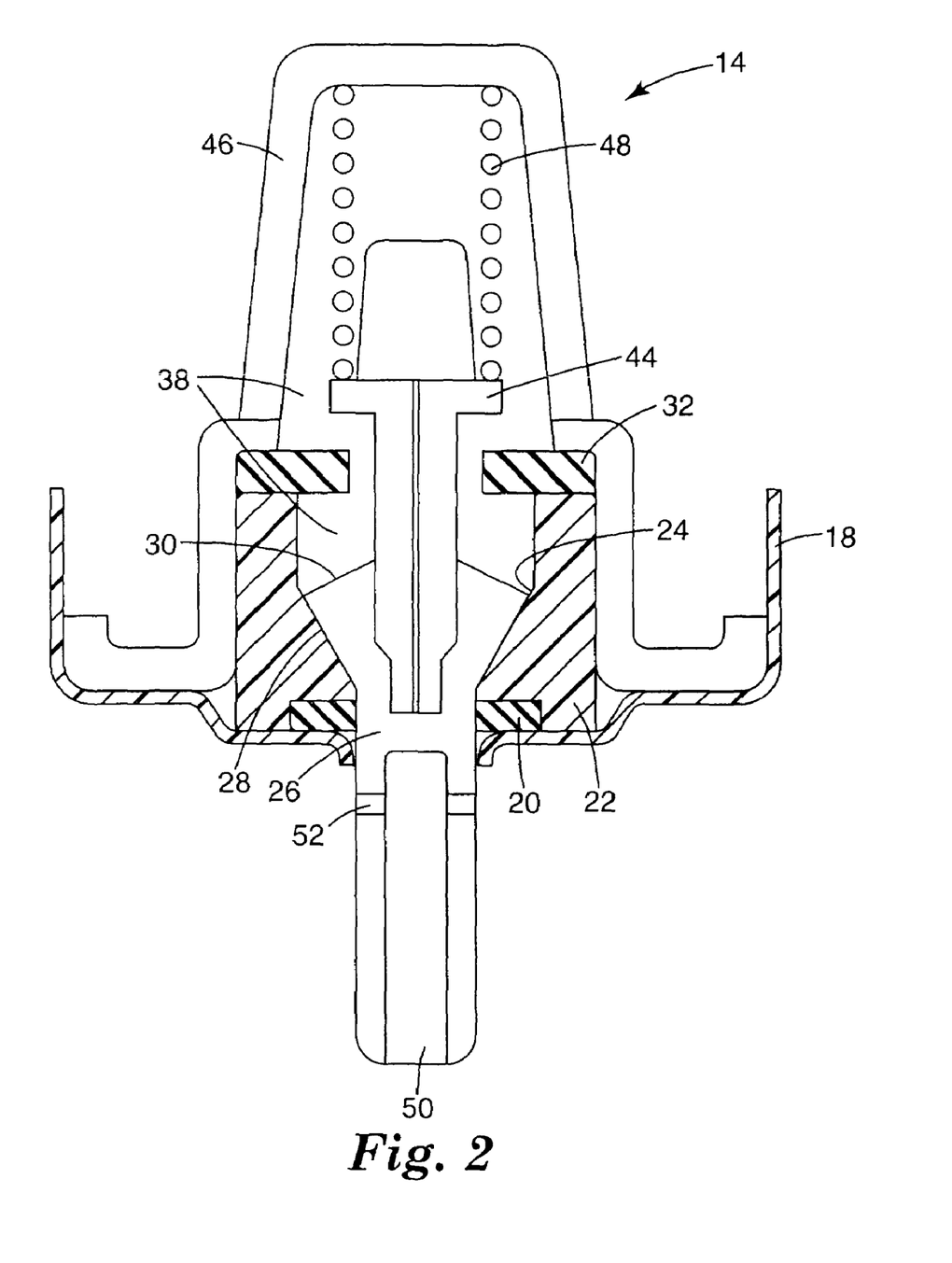
FIG. 2 is an enlarged cross-sectional view of one embodiment of another aerosol metering valve according to the present invention in the resting position.

Referring to FIG. 2 showing an embodiment of a metering valve 14 (in the resting position), the metering valve 14 typically includes a housing 18 that serves to house the various components of the metering valve 14. The top portion of the housing 18 attaches to the aerosol container 12 (as exemplarily shown in FIG. 1). A valve body 22, typically seated within the valve housing 18, in turn provides a housing for a valve stem 26. The valve body 22 includes an interior surface 24 defining an internal chamber or cavity of the valve body.

The metering valve 14 typically includes a spring cage 46 that, together with the valve body 22, defines an interior chamber 38, a portion of which is occupied by a portion of the valve stem 26. One or more inlets (not shown) typically traversing the spring cage provide open and unrestricted fluid communication between the interior chamber 38 and the aerosol container 12.

The valve stem 26 includes two portions, a body portion and a stem portion. The stem portion includes that portion of the valve stem that is outside the valve housing 18 when the valve stem 26 is in the resting position shown in FIG. 2. During actuation of the valve stem 26, however, the stem portion will be displaced inwardly with respect to the metering valve 14, as described more fully below, so that some of the stem portion will be transiently positioned inside the valve housing 18. The stem portion includes a passageway 50 through which a metered dose of formulation is discharged, as will be described more fully below. The passageway includes one or more side holes 52.

The body portion of the valve stem 26 is that portion that is positioned within the valve housing 18 throughout actuation of the valve stem 26. The body portion of the valve stem 26 (as shown in FIGS. 2-5) includes a metering surface 28 and a sealing surface 30.

The body portion of the valve stem 26 is configured to have substantially the same shape as the surrounding wall of the valve body 22. Thus, as can be seen in the embodiment shown in FIG. 2, a substantial portion of the metering surface 28 of valve stem 26 rests in contact with the interior surface of the valve body 24 when the metering valve is in the resting position, thereby minimizing, if not eliminating, the annular gap between the valve stem and valve body when the metering valve is in the resting position, and thus minimizing, if not eliminating, residual metering volume.

The metering valve may include a spring guide 44 mounted on the end of the valve stem body portion opposite the stem portion and a spring 48 within the interior chamber 38 of the metering valve as shown in FIG. 2. The spring 48 through engagement with the spring guide biases the valve stem 26 toward the resting position. It will be appreciated by those skilled in the art that any suitable means for biasing the valve stem 26 into the resting position, e.g. coil compression spring or a spring appropriately mounted external to the interior chamber, may be used in connection with metering valves according to the present invention. The spring guide may be an integral part of the valve stem and/or arranged to include a pressure filling ring as described in the U.S. Pat. No. 5,400,920, which is incorporated by reference herein.

The metering valve 14 also includes at least two annular gaskets, the diaphragm 20 and the metering gasket 32. The diaphragm 20 is positioned between the valve housing 18, the valve body 22 and the valve stem 26, as shown in FIG. 2. The diaphragm 20 isolates the formulation in the aerosol container 12 from the exterior of the valve by forming two fluid tight seals: 1) an annular sliding seal between the diaphragm 20 and the valve stem 26 where the valve stem extends out of the valve housing, and 2) two compressive planar or face seals between the valve body 22, the diaphragm 20 and the housing 18. The latter seal may be effected either with or without a sealing bead on either the valve body 22 or the housing 18.

In the embodiment shown in FIGS. 2-5, the metering gasket 32 is included in the body wall of the valve body, being generally positioned between the valve body 22, the spring cage 46, and the body portion of the valve stem 26. The metering gasket 32 forms two fluid tight compressive planar or face seals between the metering gasket 32 and the valve body 22 and the spring cage 46. These may be achieved either with or without a sealing bead on the valve body 22 and/or the spring cage 46.

The metering gasket in this embodiment or other embodiments in accordance with the present invention may be either mechanically affixed, molded onto the respective component of the metering valve, or the respective components may be manufactured using, for example, a two shot or co-molding process in which the corresponding component of the metering valve and metering gasket are co-molded so that a strong bond (mechanical and/or chemical) can be achieved between the components.

Figure 4:
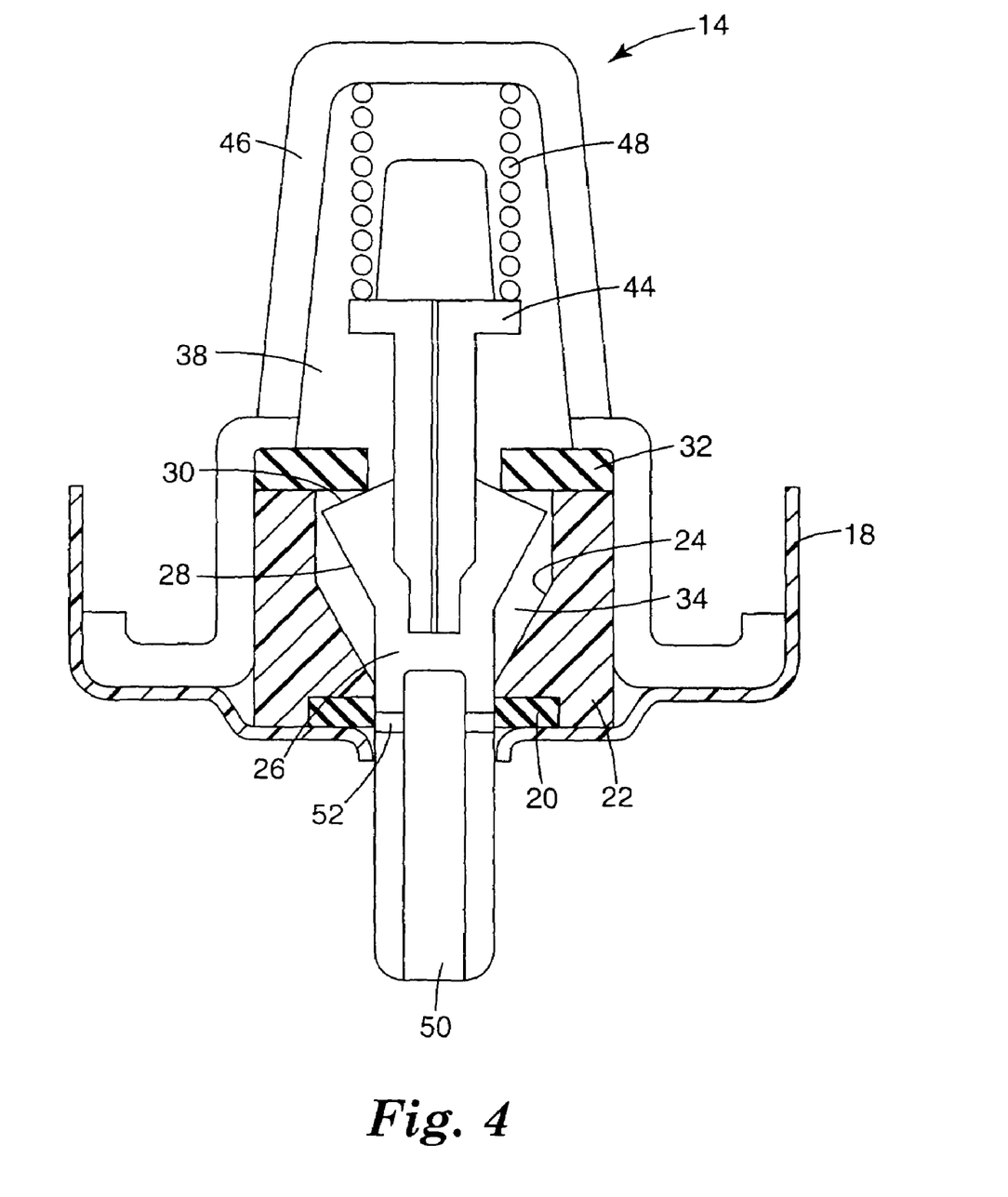
FIG. 4 is an enlarged cross-sectional view of the aerosol metering valve shown in FIG. 2 at the filled stage of valve stem actuation.

As shown in FIG. 4, the metering gasket 32 transiently isolates the formulation in the metering chamber 34 from the aerosol container 12 by forming a fluid-tight face seal between the metering gasket 32 and the sealing surface 30 of the valve stem 26. The metering gasket 32 provides a means for terminating the flow of formulation from the aerosol container 12 to the metering chamber 34 during actuation of the valve stem 26, as will be described in more detail below.

Figure 3:
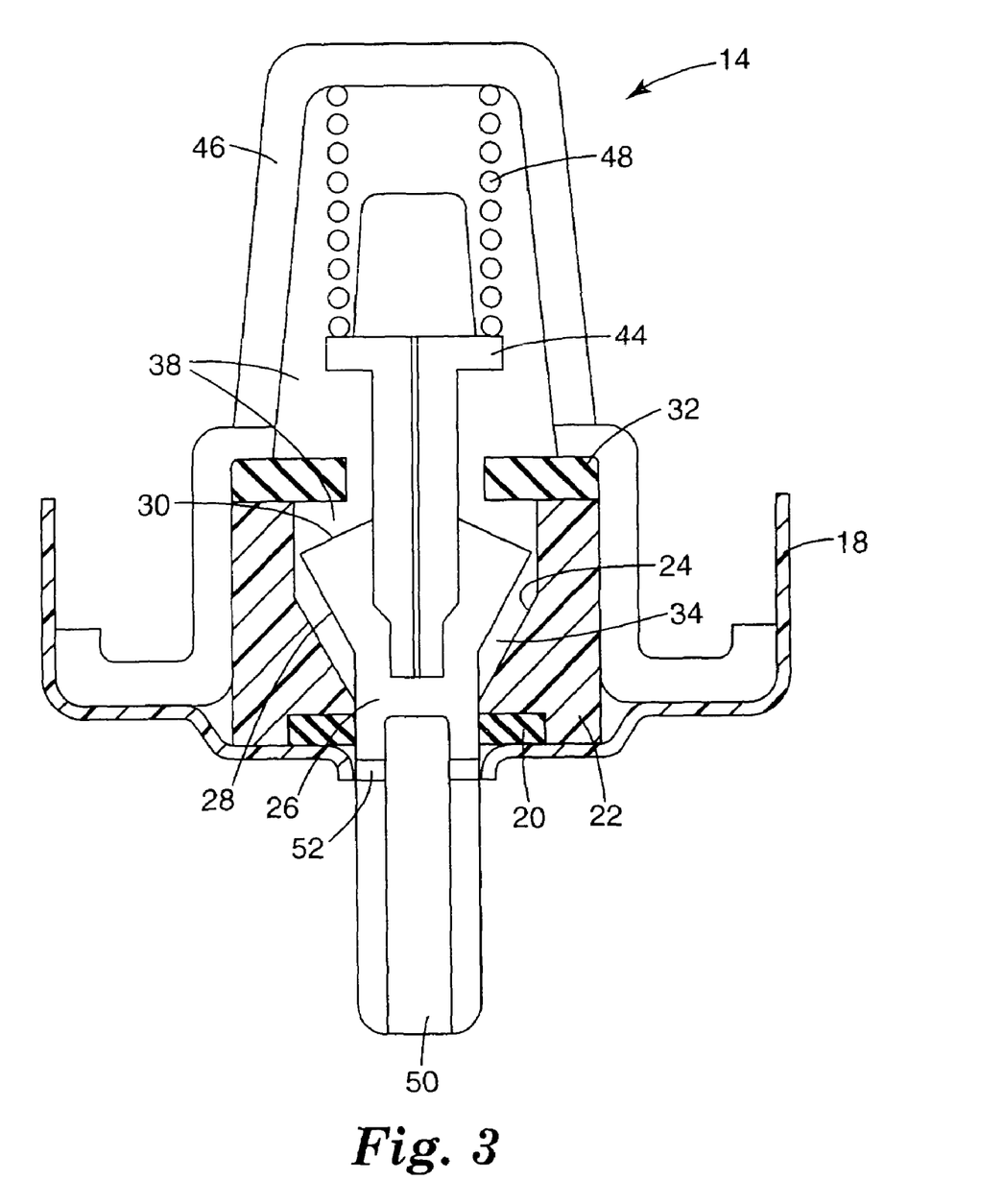
FIG. 3 is an enlarged cross-sectional view of the aerosol metering valve shown in FIG. 2 during the filling stage of valve stem actuation.
Figure 5:
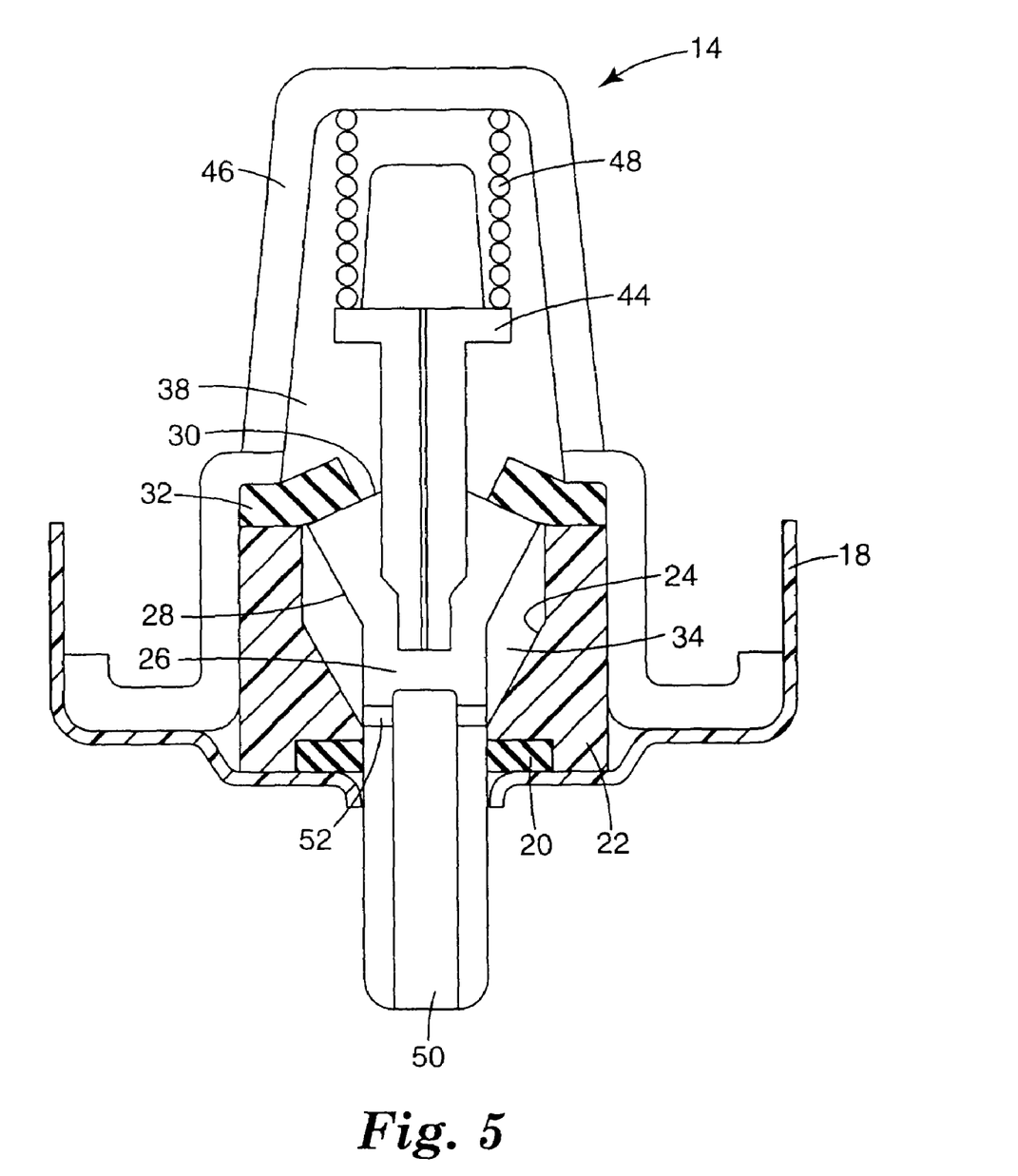
FIG. 5 is an enlarged cross-sectional view of the aerosol metering valve shown in FIG. 2 during the discharge stage of valve stem actuation.

Operation of the metering valve 14 shown in FIG. 2 is illustrated in FIGS. 3, 4 and 5. The figures illustrate the stages of operation of the metering valve 14 and the corresponding relative positions of the valve components as a patient actuates the valve stem 26, thereby releasing a dose of aerosol formulation. FIG. 3 shows the metering valve 14 in the filling stage, FIG. 4 shows the metering valve 14 in the filled stage, and FIG. 5 shows the metering valve 14 in the discharge stage.

As can be seen in FIG. 3 during the filling stage of actuation, the valve stem 26 has been displaced inwardly into the interior chamber 38 against the compressive force of the spring 48. As the valve stem 26 is displaced inwardly, the proximal end of the stem portion of the valve stem 26 enters the valve housing 18. As a result, a metering chamber 34 is formed between the interior surface of the valve body 24 and the metering surface 28 of the valve stem 26. The volume of the metering chamber 34 increases as the valve stem is displaced until it reaches its filled-volume at the end of the filling stage as depicted in FIG. 4 showing the completely filled position.

Aerosol formulation enters the filling volume of the metering chamber 34 in the following manner. Formulation from the aerosol container 12 passes through the one or more inlets and into the interior chamber 38 of the metering valve. From the interior chamber 38, the formulation passes between the spring guide 44 and the metering gasket 32. Formulation flows around the proximal end of the valve stem 26 between the valve stem 26 and the interior surface of the valve body 24 and enters the expanding metering chamber 34. The spring guide may be provided with cutaway portions or openings to improve flow and/or access to the metering chamber.

Thus, as the valve stem 26 is moved from the resting position shown in FIG. 2 to the filling stage shown in FIG. 3, aerosol formulation passes from the aerosol container 12 to the metering chamber 34 immediately upon actuation of the valve stem 26. Formulation continues to fill the metering chamber 34 until the metering valve 14 reaches the filled stage as depicted in FIG. 4. As will be described in more detail below, the flow of formulation into the metering chamber 34 may be affected by the angle described by the metering surface of the valve stem 28 with respect to the central longitudinal axis of the valve stem.

At the end of the filling stage, the flow path of formulation from the aerosol container 12 to the metering chamber 34 is cut off as the metering gasket 32 contacts the sealing surface 30 of the valve stem 26, as can be seen in FIG. 4. The metering gasket 32 forms a fluid-tight, face seal with the sealing surface 30, thereby concluding filling of the metering chamber 34 and isolating the metering chamber prior to discharge. The sealing surface 30 may be provided with a sealing bead and may be any shape suitable for providing desired sealing characteristics. However, for enhanced sealing performance and valve operation, as discussed in more detail below, the sealing surface 30 is desirably generally conical and more particularly in its longitudinal cross-section the sides may be either substantially straight-edged (as shown in e.g. FIG. 4) or concave (as shown in e.g. FIG. 6).

At this stage, the metered dose of formulation is isolated and ready for discharge from the metering chamber 34 and delivery to the patient. The dimensions of the valve body 22, valve stem 26 and other valve components determine the filled-volume of the metering chamber 35 in the completely filled position.

FIG. 5 depicts the metering valve 14 in the discharge stage of actuation. In order to discharge the metered dose of aerosol formulation from the metering chamber 34, the valve stem 26 is further actuated to the position illustrated in FIG. 5. Those skilled in the art will realize that the distance traveled by the valve stem 26 between FIG. 4 and FIG. 5 will result in an expansion of the metering chamber 34 without increasing the metered dose. The extra travel ensures that the metering gasket 32 is sealed against the sealing surface 30 before the one or more side holes 52 enter the metering chamber 34. As can be appreciated from FIGS. 4 and 5, as the valve stem is further actuated from the completely filled-position (as shown in FIG. 4) to the discharge position (illustrated in FIG. 5), the metering gasket 32 stretches and the facing contact surfaces of the metering gasket and the sealing surface 30 show a relative movement to one another in reciprocation of the travel of the valve stem. Thus the face seal here may be considered a dynamic, reciprocating face seal. As the valve stem 26 is fully actuated, the one or more side holes 52 of the discharge passageway 50 pass through the diaphragm 20 and come into fluid communication with the metering chamber 34. The fluid communication thus established allows the aerosol formulation within the metering chamber 34 to be released into the one or more side holes 52 and the formulation thus passes through the discharge passageway 50, thereby delivering the metered dose of aerosol formulation to the patient or other desired area.

During the discharge of the aerosol formulation from the metering chamber 34 as shown in FIG. 5, the metering gasket 32 continues to prevent the passage of additional bulk formulation from the aerosol container 12 to the metering chamber 34, with allowance made for the dimensional tolerances of the valve components. After the dose of aerosol formulation is discharged, the patient releases the valve stem 26, which returns to its original resting position depicted in FIG. 2 by at least the biasing action of the spring 48. In some embodiments, the metering gasket 32 also may provide biasing action that promotes return of the valve stem 26 to the resting position.

The successive stages of valve stem actuation, as exemplarily depicted in FIGS. 3, 4 and 5, are all accomplished during the brief duration of actuation of the valve stem. Accordingly, formation, filling and emptying of the metering chamber occurs rapidly. At most, only a very small percentage of a dose of formulation resides in the metering chamber between actuations. In some embodiments, the metering chamber may not exist at all in the resting state—the residual metering volume may be zero—so that no formulation can reside in the metering chamber between actuations. Because the stages of valve stem actuation occur rapidly, the metering chamber is full of formulation only for a brief moment immediately prior to discharge of the formulation from the metering chamber.

FIGS. 6 and 7 illustrate another embodiment of a metering valve 14 in its resting position and during discharge stage of actuation. This embodiment provides an example in which the spring guide 44 is formed of two parts, a spring guide stem 44' and a spring guide cap 44", wherein the valve stem 26 and spring guide stem are formed as a single element and the spring guide cap is formed as a separate element, which is subsequently affixed onto the spring guide stem.

In comparison to the embodiment of FIGS. 2-5, in this embodiment the body portion of the valve stem 26 is configured such that the angle described by a major portion of the metering surface 28 of the valve stem with respect to the central longitudinal axis of the valve stem is larger. During actuation of the metering valve 14, the operation of which is the same as that described for the embodiment illustrated in FIGS. 2-5, free flow of formulation during the filling stage into the metering chamber 34 formed upon actuation is further enhanced, as discussed in more detail below, due to the desirable configuration of the metering surface 28 of the body portion of the valve stem 26. The sealing surface 30 in this embodiment, similar to the sealing surface in the embodiment depicted in FIGS. 2-5, is also generally conical. This embodiment provides an example of a metering valve including a sealing surface 30, which is substantially concave in its longitudinal cross-section. As can be appreciated from FIG. 7, this configuration of the sealing surface 30 advantageously facilitates the sealing performance of metering gasket 32 against the sealing surface.

FIGS. 8 and 9 illustrate a further embodiment of a metering valve 14 in its resting position and during discharge stage of actuation. This embodiment is similar to the configured such that the angle described by a major portion of the metering surface 28 of the valve stem with respect to the central longitudinal axis of the valve stem is even greater, being about 90°, and the sealing surface 30 is generally conical with substantially straight-edged sides in its longitudinal cross-section.

The configurations of the valve body 22, valve stem 26 and in some cases other valve components influence free flow of formulation and the presence of residual metering volume when the metering valve is in its resting position as well as the flow of formulation into the metering chamber 34 when the valve stem is actuated.

For example, when the metering portion (a portion that, in part, bounds the metering chamber formed upon actuation) of the valve body is configured to substantially conform to the metering surface of the valve stem, when the metering valve is in its resting position, the presence of residual metering volume is minimized. Under the term "metering portion of the valve body is configured to substantially conform to the metering surface of the valve stem", it is desirably understood that a significant portion (e.g. ≧90%) of the metering surface of the valve stem rests in contact with the interior surface of the valve body when the metering valve is in the resting position. The residual metering volume may be further minimized, by configuring the metering portion of the valve body to essentially conform or to conform to the metering surface of the valve stem when the valve is at rest. Under the term "metering portion of the valve body is configured to essentially conform or to conform to the metering surface of the valve stem", it is desirably understood that substantially the complete portion (e.g. ≧95%) or essentially the complete portion (e.g. ≧97.5% or more desirably ≧99%), respectively, of the metering surface of the valve stem rests in contact with the interior surface of the valve body when the metering valve is in the resting position.

Free flow of formulation in the valve in its rest position may be further desirably influenced, by configuring the metering surface of the body portion of the valve stem, such that no significant portion (e.g. ≦5% or more desirably ≦2.5%), more suitably no substantial portion (e.g. ≦2% or more desirably ≦1%), or most suitably no portion of the metering surface adjacent to the interface between the metering surface and the sealing surface of the body portion of the valve body is aligned parallel or nearly parallel to the stem axis (i.e., with a very small angle θ, e.g., 0° or 1°). Also, free-flowing communication between the bulk formulation and formulation within the interior chamber, in particular in the vicinity of the body portion of the valve stem and the internal chamber or cavity of the valve body defined by the interior surface of the valve body wall, when the metering valve is in the resting position may be enhanced by certain configurations of the sealing surface of the body portion of the valve stem. In particular, it may be desirable to configure the sealing surface of the body portion of the valve stem, such that no significant portion (e.g. $\leq 5\%$ or more desirably $\leq 2.5\%$), more suitably no substantial portion (e.g. $\leq 2\%$ or more desirably $\leq 1\%$), or most suitably no portion of the sealing surface adjacent to the interface between the metering surface and the sealing surface of the body portion of the valve body is aligned parallel or nearly parallel to the stem axis.

Figure 10:
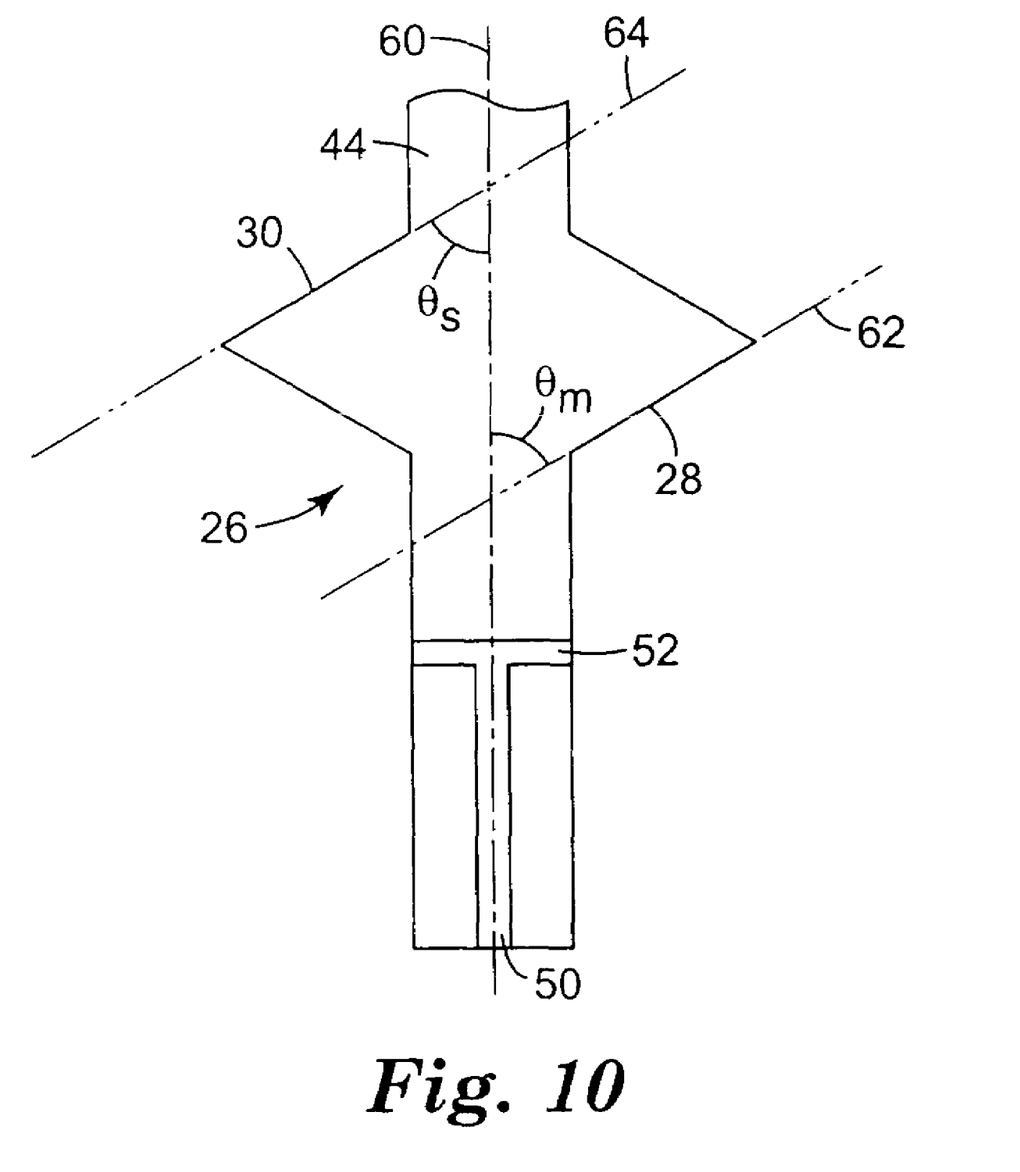
FIG. 10 is an enlarged cross-sectional view of one embodiment of a valve stem according to the present invention.
Figure 12:
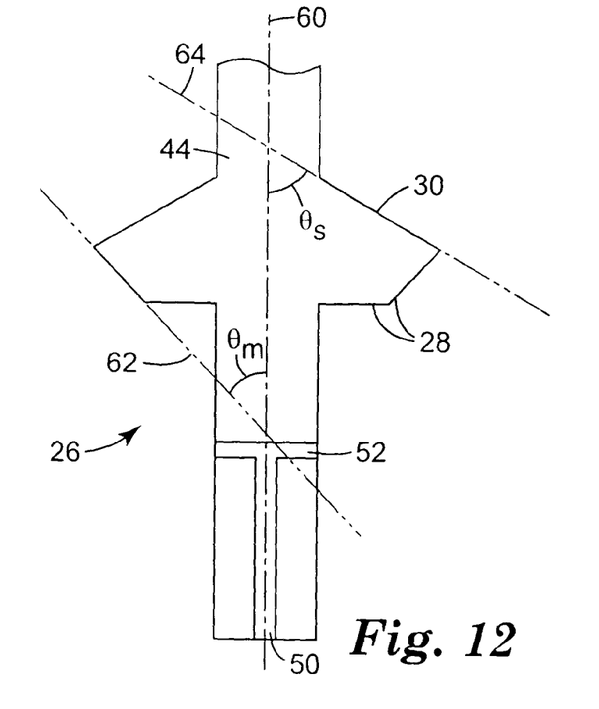
FIG. 12 is an enlarged cross-sectional view of another alternative embodiment of a valve stem according to the present invention.

As mentioned above, the flow of formulation into the metering chamber during actuation may be affected by the angle described by the metering surface of the valve stem with respect to the central longitudinal axis of the valve stem. For example, the valve stem 26 may define a central longitudinal axis 60, as shown in FIG. 10. An angle $\theta_m$ may be defined by the intersection of a plane 62 tangential to a major portion of the metering surface 28 of the valve stem and the central axis 60. In some embodiments with complex geometries, angle $\theta_m$ may be defined by the intersection of the central axis 60 and a plane tangential with a minor portion of the metering surface 28, as shown in FIG. 12.

All else being equal and assuming that the valve body is configured to substantially conform to the valve stem, a larger $\theta_m$ results in a wider filling gap for a given displacement of the valve stem during actuation of the metering valve. For given sealing diameters and a given stem displacement distance to the metering point, a larger value of $\theta_m$ generally allows the valve stem and the metering valve to be shorter. The shape of the metering surface 28 shown in FIG. 12 allows the use of a particular angle $\theta_m$ in a shorter metering valve. A simpler metering surface, such as that shown in FIG. 10, may require less dimensional control in order to manufacture the valve stem and valve body that substantially conform to one another and thereby limit or eliminate residual metering volume when the metering valve is at Suitable values for angle $\theta_m$ in valve stems according to the present invention are from about 2° to about 90°. Within this range a minimum angle of about 10° is more desirable, about 20° even more desirable and about 30° most desirable. A maximum angle of about 80° is more desirable, about 70° even more desirable and about 60° most desirable.

To limit the potential of areas of restricted flow within the metering chamber and thus enhanced free flow of formulation into the metering chamber, the metering surface is desirably configured to comprise no significant portion (e.g. ≦5% or more desirably ≦2.5%), more suitably no substantial portion (e.g. ≦2% or more desirably ≦1%), or most suitably no portion aligned parallel or nearly parallel to the stem axis.

As can be seen in the exemplary embodiments shown in FIGS. 2, 6 and 8, the body portion of the valve stem typically includes a section adjacent to the stem portion, which is aligned parallel or nearly parallel to the stem axis. This section facilitates the passage of the valve stem through the opening of the valve housing and/or the diaphragm. Because this section is adjacent to the stem portion and at the distal end of the metering chamber formed upon actuation (as can be appreciated for example in FIG. 3), a parallel or nearly parallel alignment of this section of body portion does not restrict the flow into the metering chamber.

As can be best seen in FIGS. 10 to 12 showing exemplary valve stems, the metering surface 28 is typically that surface of the section of the body portion located between the section of the body portion comprising the sealing surface 30 and the section of the body portion adjacent to the stem portion being aligned parallel or nearly parallel to the stem axis. The circumferential interface or boundary of the metering surface and the sealing surface may generally be understood to be the annulus of widest transverse cross section of the valve stem body. In embodiments, which in accordance to the aforesaid definition would have an interface or boundary having a portion parallel to the longitudinal axis of the stem, the interface or boundary is typically understood in this case to be the annulus at the proximal end of the parallel portion (i.e. the end distant from the stem portion). As can be appreciated from FIGS. 10 to 12, if the valve stem includes a mounted or integral spring guide 44, the sealing surface 30 typically ends at the interface or boundary between the surface of the body portion of the valve stem and the surface of the spring guide.

The sealing characteristics and/or the flow of formulation into the metering chamber during actuation and/or free flow of formulation when the metering valve is at rest may also be affected by configuration of the sealing surface, and as mentioned above, the sealing surface 30 is desirably generally conical and more particularly in its longitudinal cross-section the sides are either substantially straight-edged or concave. The angle described by the sealing surface of the valve stem with respect to the central longitudinal axis of the valve stem may also have an effect.

Referring to FIG. 10, an angle θS may be defined by the intersection of a plane 64 tangential to a major portion of the sealing surface 30 of the valve stem and the central axis 60. Typical values for angle θs may be from about 30° to about 80°. Within this range, a minimum angle of about 35° is more desirable and about 40° most desirable. A maximum angle of about 75° is more desirable and about 70° most desirable. In some embodiments, angle $\theta_s$ may be defined by the intersection of the central axis 60 and a plane tangential with a minor portion of the sealing surface 30. For embodiments in which the sealing surface is generally conical in form with concave sides in its longitudinal cross-section, angles of $\theta_s$ may be defined along the entire concave surface by the intersection of the central axis 60 and planes tangential to the curved surface; the values of these angles are desirably all within the ranges defined above.

Metering valves having an angle $\theta_m$ in the ranges described may have a metering portion—a portion that, in part, bounds the metering chamber—that can generally be described as conical in shape with a cross-sectional area of the proximal portion of the cone being greater than the cross-sectional area of the distal portion of the cone. In some embodiments, the transverse cross-sectional area of the valve stem body at the metering and sealing surface interface may be about 4% greater than the transverse cross-sectional area of the distal end (i.e. towards the stem portion of the valve stem) of the valve stem body. In other embodiments, the transverse cross-sectional area of the valve stem body at the metering and sealing surface interface may be at least about 20% greater than the transverse cross-sectional area of the distal end of the valve stem body. In still other embodiments, the transverse cross-sectional area of the valve stem body at the metering and sealing surface interface may be at least about 60% greater than the transverse cross-sectional area of the distal end of the valve stem body.

In certain embodiments having a generally conical metering portion, the interior surface of the valve body maintains a generally conical form from the diaphragm to the valve body sealing surface.

Figure 11:
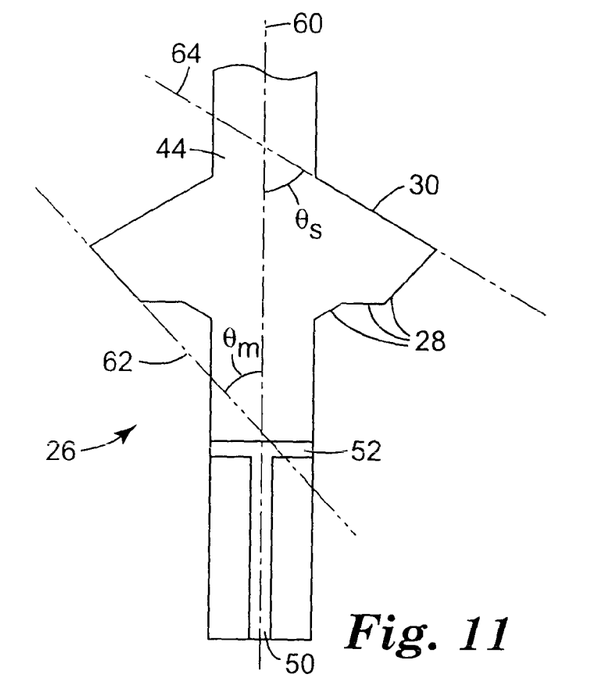
FIG. 11 is an enlarged cross-sectional view of an alternative embodiment of a valve stem according to the present invention.

The metering surface 28 of the valve stem 26 may be of any suitable configuration and still define the plane 62 used to define angle $\theta_m$. For example, in a valve stem having relatively simple geometry, such as the valve stem shown in FIG. 10, a majority of the metering surface 28 may define the plane 62 used to define angle $\theta_m$. Alternatively, the metering surface 28 may be irregular, such as is shown in FIGS. 11 and 12, and only a portion of the metering surface may be used to define the plane 62. Additionally, irregularities in the metering surface 28 may be non-geometrical and still provide a suitable configuration for valve stem 26 according to the present invention.

Thus, the particular geometry of the metering surface 28 is not critical so long as (1) angle $\theta_m$ can be defined as described herein, (2) the interior surface 24 of the valve body 22 is configured to substantially conform to the geometry of the metering surface 28. These factors contribute to limiting or eliminating residual metering volume when the metering valve is at rest and facilitate the reduction of restriction of the flow of formulation to the metering chamber. Furthermore, it may be advantageous for limiting or eliminating residual metering volume that no significant portion of the metering surface and/or the sealing surface adjacent to the interface between the metering surface and the sealing surface is aligned parallel or nearly parallel to the stem axis. The metering surface may be configured to have no significant or substantial portion or more desirably, no portion aligned parallel or nearly parallel to the stem axis. This may contribute to limiting the formation of areas of restricted flow within the metering chamber and thus restriction on the free flow of formulation into the metering chamber even though the interior surface 24 of the valve body 22 substantially conforms to the geometry of the metering surface 28.

Simple geometries for the metering surface 28 and the interior surface 24 of the valve body may provide certain manufacturing advantages. For example, valve stems having complete 360° rotational symmetry require no rotational alignment during valve assembly. Simple shapes such as cones might also confer certain performance advantages. For example, simple shapes may reduce problems with deposition of drug or with formulation flow discontinuities at angular edges. However, more complex geometries also are suitable for valve stems 26 according to the present invention. For example, some embodiments may include hemispherical or other curved configurations. Other embodiments may include valve stems having multiple angles, such as those shown in FIGS. 11 and 12.

The design of the metering surfaces according to the present invention may contribute, along with other aspects of metering valve or valve stem design, to improve the flow of formulation through the metering valve during actuation. Accordingly, the designs of the present invention may be used in conjunction with general metering valve designs other than those explicitly shown in the Figures. Such alternative metering valve designs may include one or more additional features of the valve stem, valve body, or any other portion of the metering valve designed to improve performance of the metering valve. Such additional design features may improve metering valve performance by improving performance parameters including but not limited to formulation flow from the aerosol container to the metering chamber during actuation and consistency of formulation metering.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An aerosol metering valve comprising:
   (a) a valve stem that generally defines a longitudinal axis and comprises:
      (1) a body portion comprising a proximal end, a distal end, and at least one side surface connecting the proximal end and the distal end and comprising a metering surface, and
      (2) a stem portion comprising a discharge passageway;
   (b) a valve body comprising:
      (1) a body wall that comprises a sealing portion,
      (2) an internal chamber defined at least in part by the body wall and comprising a metering portion configured to substantially conform to the metering surface of the valve stem, and
      (3) a diaphragm having walls that define an aperture in slidable, sealing engagement with the stem portion of the valve stem; and
   (c) a metering gasket configured to be able to form a transient, substantially fluid-tight face seal between the valve stem and the sealing portion of the body wall;
   wherein a substantial portion of the metering surface of the valve stem is in contact with the metering portion of the internal chamber body wall when the valve stem is in a resting position.

2. An aerosol metering valve according to claim 1, wherein the body wall sealing portion comprises the metering gasket, which is configured to be able to form a transient, substantially fluid-tight face seal with at least a portion of the proximal end of the valve stem body.

3. An aerosol metering valve according to claim 2, wherein the body portion of the valve stem comprises a sealing surface adjacent to the metering surface and distant from the stem portion of the valve stem and wherein said sealing surface and the metering surface form a circumferential interface on the surface of the valve stem body portion.

4. An aerosol metering valve according to claim 3, wherein no significant portion of the metering surface and/or the sealing surface of the valve stem adjacent to the interface between the metering surface and the sealing surface is aligned parallel or nearly parallel to the longitudinal axis.

5. An aerosol metering valve according to claim 3, wherein the sealing surface is generally conical or conical.

6. An aerosol metering valve according to claim 5, wherein the sides of the sealing surface in its longitudinal cross-section are substantially straight-edged or straight-edged.

7. An aerosol metering valve according to claim 5, wherein the sides of the sealing surface in its longitudinal cross-section are substantially concave or concave.

8. An aerosol metering valve according to claim 3, wherein the longitudinal axis and a plane tangential to at least a portion of the sealing surface define an angle from about 30° to about 80°.

9. An aerosol metering valve according to claim 1, wherein the metering surface is generally conical or conical.

10. An aerosol metering valve according to claim 1, wherein the metering surface comprises no significant portion aligned parallel or nearly parallel to the longitudinal axis.

11. A metered dose dispensing device comprising an aerosol metering valve according to claim 1.

12. A metered dose dispensing device according to claim 11, wherein said metered dose dispensing device is a metered dose inhaler.

13. An aerosol metering valve according to claim 1, wherein the longitudinal axis and a plane tangential to at least a portion of the metering surface define an angle from about 2° to about 90°.

14. An aerosol metering valve according claim 13, wherein the angle of the metering surface is equal to or greater than about 10°.

15. An aerosol metering valve according to claim 13, wherein the angle of metering surface is equal to or greater than about 20°.

16. An aerosol metering valve according to claim 13, wherein the angle of metering surface is equal to or greater than about 30°.

17. An aerosol metering valve according to claim 13, wherein the angle of metering surface is equal to or less than about 80°.

18. An aerosol metering valve according to claim 13, wherein the angle of metering surface is equal to or less than about 70°.

19. An aerosol metering valve according to claim 13, wherein the angle of metering surface is equal to or less than about 60°.

* * * * *

UNITED STATES PATENT AND TRADEMARK OFFICE
CERTIFICATE OF CORRECTION

| | | |
|---|---|---|
| PATENT NO. | : 7,299,801 B2 | Page 1 of 1 |
| APPLICATION NO. | : 10/655419 | |
| DATED | : November 27, 2007 | |
| INVENTOR(S) | : Peter D. Hodson | |

It is certified that error appears in the above-identified patent and that said Letters Patent is hereby corrected as shown below:

*Col. 4, Line 34: After "of" insert -- illustration. The valve stems shown in isolation may be combined with one or more --.

*Col. 7, Line 5: Delete "35" and insert -- 34 --, therefor.

Figure 6:
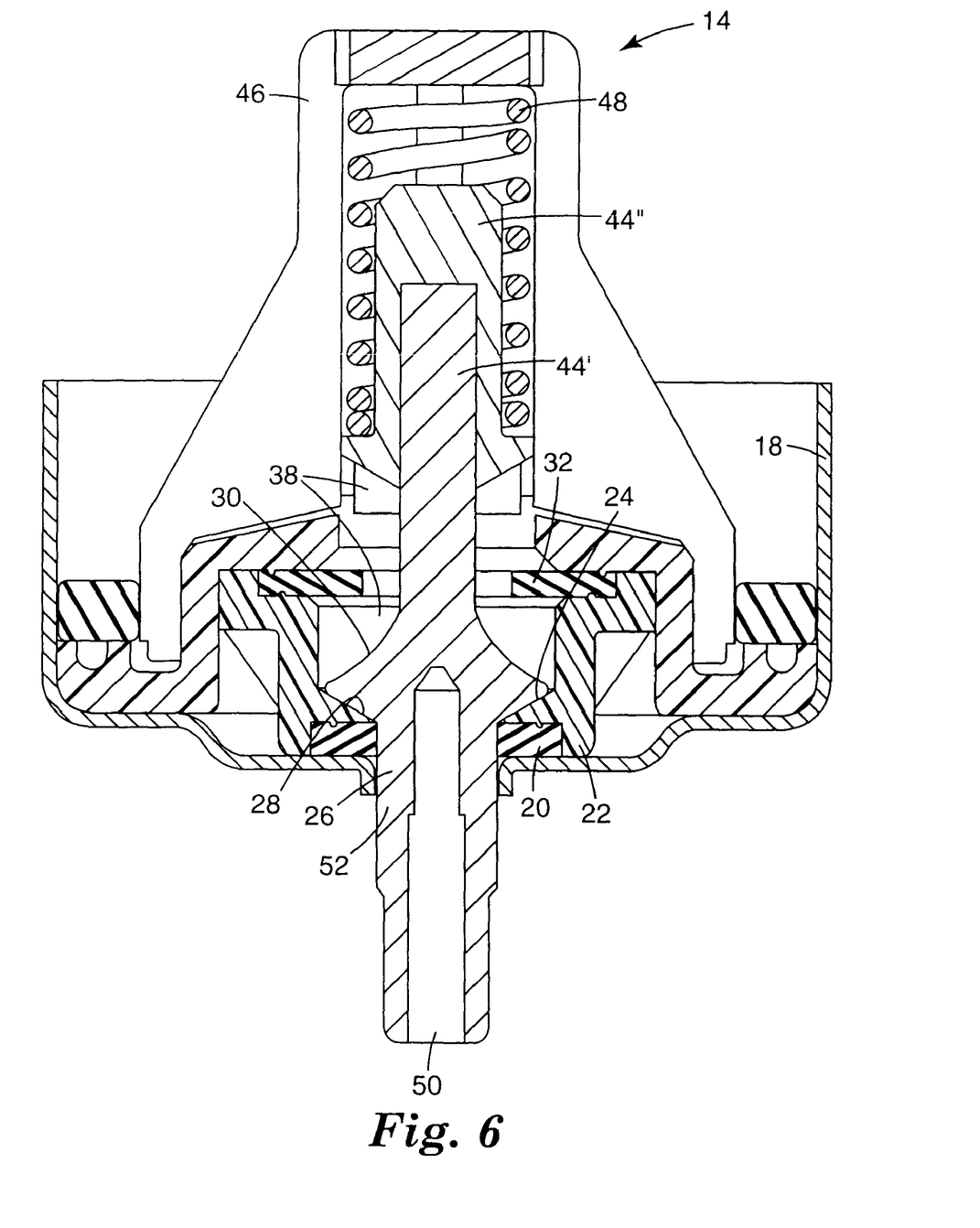
FIGS. 6 and 7 are enlarged cross-sectional views of the embodiment of an aerosol metering valve shown in FIG. 1 in the resting position and during the discharge stage of the valve stem actuation, respectively.
Figure 7:
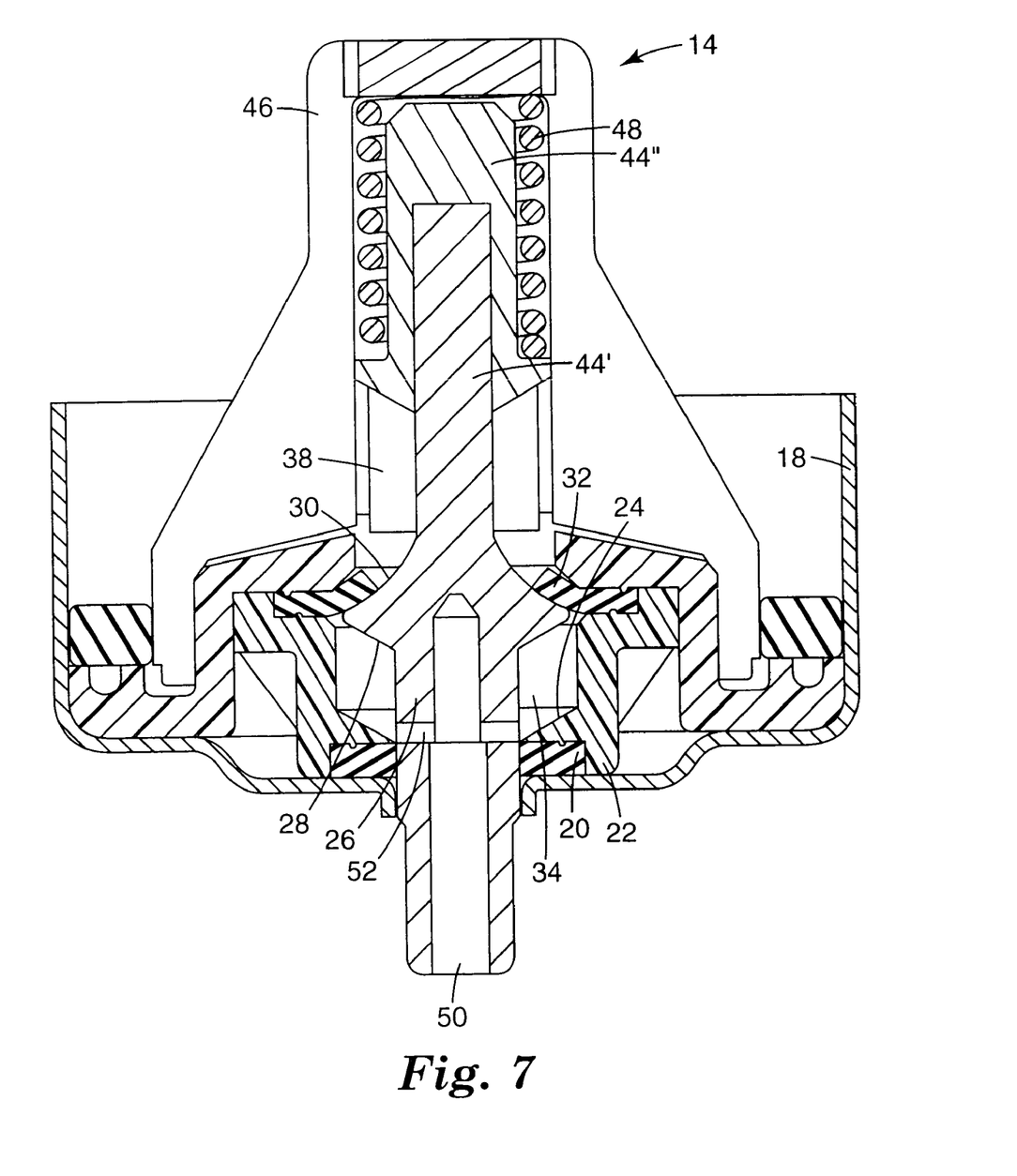
Figure 8:
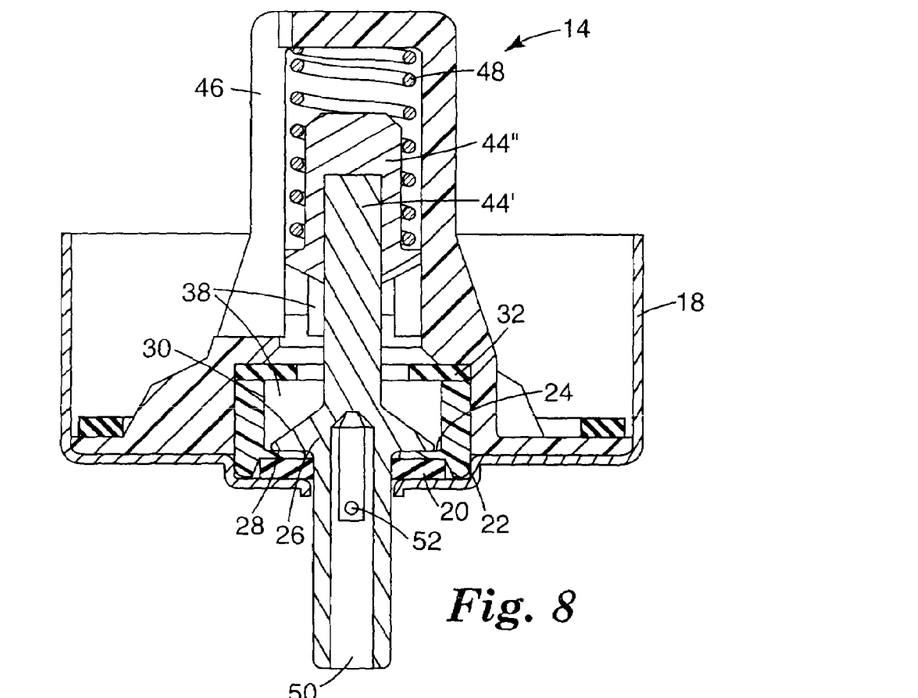
FIGS. 8 and 9 are enlarged cross-sectional views of a further embodiment of an aerosol metering valve according to the present invention in the resting position and during the discharge stage of the valve stem actuation.
Figure 9:
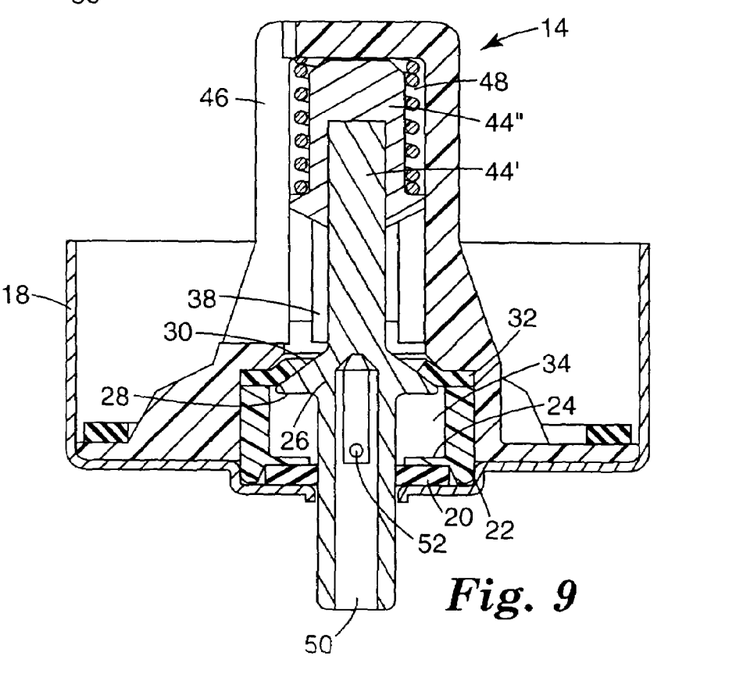

*Col. 8, Line 24: After "the" insert -- embodiment shown in FIGS. 6 and 7. Here the body portion of the valve stem 26 is --.

*Col. 9, Line 46: After "at" insert -- rest. --.

*Col. 9, Line 46-51: After "at" delete "Suitable values for angle............................most desirable." and insert the same on Col. 9, Line 47 as a new paragraph.

*Col. 10, Line 35(Approx): Delete "θS" and insert -- $\theta_S$ --, therefor.

*Col. 10, Line 38: Delete "θs" and insert -- $\theta_s$-- , therefor.

*Col. 11, Line 9: after "$\theta_m$" insert -- . --.

Signed and Sealed this

Twenty Second Day of April, 2008

JON W. DUDAS
*Director of the United States Patent and Trademark Office*